US00PP08146P

United States Patent [19]

Holtkamp, Sr.

[11] Patent Number: Plant 8,146

[45] Date of Patent: Feb. 16, 1993

[54] AFRICAN VIOLET PLANT NAMED LITTLE CHEYENNE GIRL

[76] Inventor: Reinhold Holtkamp, Sr., Blumenstrasse 28, D 4242 Rees-Haffen, Fed. Rep. of Germany

[21] Appl. No.: 736,219

[22] Filed: Jul. 26, 1991

[51] Int. Cl.[5] ..... A01H 5/00

[52] U.S. Cl. ..... Plt./69.2

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Little Cheyenne Girl characterized by its mid-size growth habit (13–15 cm in diameter); blue and white variegated, semi-double flowers having 8–12 petals, the ones in the center being much smaller and occasionally covering up the anthers; strong stems which curve toward the center to form a compact bouquet above the leaves; profuse flowering; bright green, spear-shaped, slightly serrated leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Cheyenne Girl.

The new cultivar was referred to during the breeding and selection process by the designation M/I 484 and is a sport of Little Diamond, disclosed in my U.S. Plant Pat. No. 6,918. Little Cheyenne Girl is similar in all essential respects to Little Diamond except for its larger size and bi-color, blue and white, blossom.

Little Cheyenne Girl was discovered in a flowering block of the parent cultivar Little Diamond and subsequently selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Cheyenne Girl has not been observed under all possible environmental conditions. The phenotype may vary significantly with variations in environment such as temperature, light intensity and day length. The following observations, measurements and values describe the new cultivar as grown in a 5.5 cm pot in Haffen, West Germany and Nashville, Tenn. under greenhouse conditions which closely approximate those generally used in commercial practice.

The following traits have been repeatedly observed and are determined to be basic characteristics of Little Cheyenne Girl, which in combination distinguish this African violet as a new and distinct cultivar:

(1) A single crown will not grow larger than 13–15 cm.

(2) Semi-double, blue and white variegated flowers.

(3) Strong, wirelike and upright flower stems curving toward the center.

(4) First flash of flowers forms a tight bouquet above the leaves.

(5) Profuse flowering.

(6) Each plant carries 7–9 and more upright flower stems each of which carries 6–7 and more flowers.

(7) Long lasting, non-dropping flowers.

(8) Plant saleable 10 to 11 weeks after planting of unrooted shoot.

(9) Seed capsules push slightly through.

(10) Bright green, hairy leaves.

(11) Spear-shaped leaves are 2.5 to 3.5 cm in size.

(12) After maturity the flowers dry off, and remain on the peduncle without becoming infected by botrytis.

The accompanying color photographic drawing shows a typical specimen plant of the new cultivar grown in a 5.5 cm pot. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 12 p.m. in Nashville, Tenn.

Botanical Classification: *Saintpaulia ionantha,* Ramat., c.v. Little Cheyenne Girl.

Parentage: Sport of Little Diamond, disclosed in U.S. Plant Pat. No. 6,918.

Propagation: The new cultivar holds its distinguishing characteristics through successive propagations by leaf cuttings.

Plant: From 6 cm to 8 cm tall when grown in pots, and 13–15 cm in diameter when fully grown.

Leaves:

*General form.*—Spear-shaped.

*Diameter.*—25–30 mm wide and 30–35 mm long.

*Texture.*—Leatherlike.

*Aspect.*—Shiny, hairy, slightly serrated.

*Veins.*—Upperside: visible; underside: well pronounced, light green, shiny.

*Color (upperside).*—Between Yellow-Green Group 147 A and 146 A.

*Color (underside).*—Greyed-Green Group 194 C.

*Petiole.*—Strong, green, hairy.

Flowers:

*Buds.*—Size: 5–6 mm just before opening. Shape: Ball-shaped. Color: Light green with purplish blue touch.

*Sepals.*—Five (5). Color: Brownish green.

*Calyx.*—Shape: Funnel-shaped. Aspect: Spear-shaped, hairy.

*Peduncle.*—Character: Strong upright, hairy. Color: Green with brownish touch.

Individual flowers:

*Size.*—27–32 mm.

*Shape.*—Semi-double, 8–12 petals per flower. Occasionally the 2–3 small petals in the center cover up the anthers.

*Color (underside).*—Bi-color: blue and white variegated with the blue being Violet-Blue 93 B in the center, fading to Violet-Blue 89 C to D on the petals. Under cooler temperatures and more intensive lighting, the purplish blue tends to intensify.

*Color (underside).*—White with touches of Violet Group 88 D.

*Borne.*—Each flower stem carries 6–7 and more flowers on strong, upright peduncles that are free standing above the leaves, thereby forming a compact bouquet.

*Flowering habit.*—Flowers 10–11 weeks after planting an unrooted plantlet.

Reproductive organs:

*Stamens.*—Two (2). Anthers: 2 composed of 4 anther cells, seed capsule pushes slightly through.

*Filaments.*—Yellowish green with purplish blue touch on edges, 2–3 mm long.

*Styles.*—5–6 mm long, purplish blue, base of ovary light green and hairy.

Roots: Normally developed, white when young, turning slightly brownish when older.

Disease resistance: Up to date, Little Cheyenne Girl has shown very good resistance to all major violet diseases.

GENERAL OBSERVATIONS

Little Cheyenne Girl is a mid-size violet, a size between a regular violet (grown in a 10 cm pot) and a superminiature (grown in a 4 cm pot). Little Cheyenne Girl is designed to be grown in a 5.5 cm to 6 cm pot and will not grow larger than 13–15 cm. It is very attractive due to its blue and white variegated flowers. The semi-double flowers are composed of 8–12 petals, the ones in the center being much smaller and occasionally covering up the anthers. The flowers are long-lasting and non-dropping. A nice bouquet of flowers free standing above the leaves develops 10–11 weeks after planting an unrooted plantlet. Each of the 7–9 and more strong flower stems carries 6–7 and more flowers. The bright green leaves are spear-shaped and slightly serrated.

I claim:

1. A new and distinct cultivar of African violet named Little Cheyenne Girl, as described and illustrated, and particularly characterized by its mid-size growth habit (13–15 cm in diameter); blue and white variegated, semi-double flowers having 8–12 petals, the ones in the center being much smaller and occasionally covering up the anthers; strong stems which curve toward the center to form a compact bouquet above the leaves; profuse flowering; bright green, spear-shaped, slightly serrated leaves; flowering 10–11 weeks after planting of unrooted shoot, and by its long lasting and non-dropping flowers.

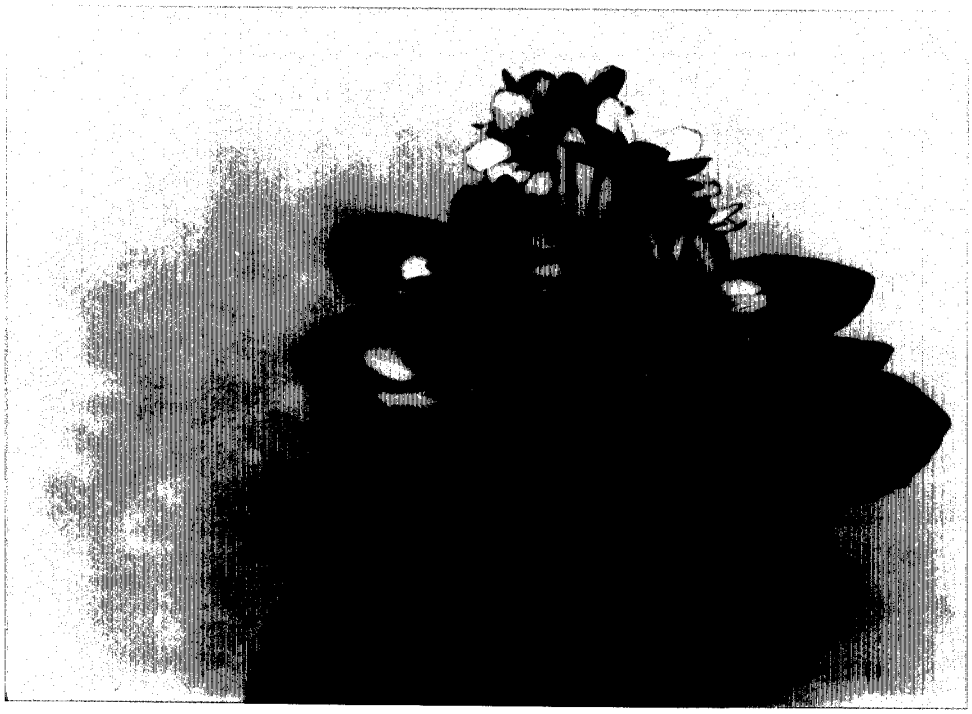

* * * * *